United States Patent [19]

Dembek

[11] Patent Number: 5,386,044

[45] Date of Patent: Jan. 31, 1995

[54] POLYHALOAROMATIC RUTHENIUM COMPLEXES AND REACTIONS THEREOF

[75] Inventor: Alexa A. Dembek, Wilmington, Del.

[73] Assignee: E. I. Du Pont de Nemours and Company, Wilmington, Del.

[21] Appl. No.: 159,152

[22] Filed: Nov. 30, 1993

[51] Int. Cl.$^6$ .................... C07F 15/00; C07F 17/02
[52] U.S. Cl. ............................ 556/13; 556/136
[58] Field of Search ........................ 556/13, 136

[56] References Cited

PUBLICATIONS

Moriarity, R. M., et al., *J. Organometal. Chem.*, 350, 157–190, 1988.
Gill, T. P., et al., *Organometallics*, 1, 485–488, 1982.
Wilkinson, G., et al., (Ed.), *Comprehensive Organometallic Chemistry*, 3, Pergamon Press, Oxford, 1001, 1982.
Wright, M. E., *Organometallics*, 8, 407–411, 1989.
Percec, V., et al., *J. Polym. Sci. A*, 31, 923–932, 1993.
Astruc, Tet., *Tet. Reports No. 157*, 39, 4037–4038, 1983.

*Primary Examiner*—José G. Dees
*Assistant Examiner*—Porfirio Nazario-Gonzalez

[57] ABSTRACT

Novel ruthenium pi-arene complexes in which the arene ring has 3 or more halogen atoms bound to it are disclosed. These compounds are reacted with phenoxides and thiophenoxides to form ruthenium pi-arene complexes of polyfunctional aromatic ethers and thioethers which are useful as monomers and crosslinking agents.

11 Claims, No Drawings

POLYHALOAROMATIC RUTHENIUM COMPLEXES AND REACTIONS THEREOF

FIELD OF THE INVENTION

Disclosed herein are novel polyhaloaromatic pi-arene complexes of ruthenium, which can react with phenoxides or thiophenoxides to form polyfunctional ruthenium complexes. Such complexes are useful as crosslinking agents in polymerizations.

TECHNICAL BACKGROUND

Ruthenium pi-arene complexes with certain aromatic compounds are known, see for instance R. M. Moriarty, et al., J. Organometal. Chem., vol. 350, p. 157–190 (1988). Such complexes in which a benzene ring contains one or two halogen atoms are known (see T. P. Gill et al., Organometallics, vol. 1, p. 485–488 (1982), and R. M. Moriarty, et al., ibid). The complexes which contain halogenated benzene rings are also known to undergo nucleophilic substitution reactions with phenoxides or thiophenoxides (R. M. Moriarty, et al., ibid).

However, to Applicant's knowledge, no pi-arene complex of ruthenium has been reported wherein the arene ring contains more than two halogen atoms. Furthermore, there are comments or experiments in the art where doubt has been expressed as to whether similar complexes with other metals (Cr, Fe) which contain 3 or more halogen atoms attached to the aromatic ring can be made, see G. Wilkinson, et al., Ed., Comprehensive Organometallic Chemistry, Vol. 3, Pergamon Press, Oxford, 1982, p. 1001; M. E. Wright, Organometallics, vol. 8, p. 407–411 (1989); V. Percec, et al., J. Polym. Sci. A, vol. 31, p. 923–932 (1993); and D. Astruc, Tet. (Tet. Reports No. 157), vol.-39, p. 4027–4095 (see especially p. 4038) (1983).

SUMMARY OF THE INVENTION

This invention concerns a pi-polyhaloarene complex of the formula

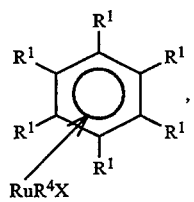

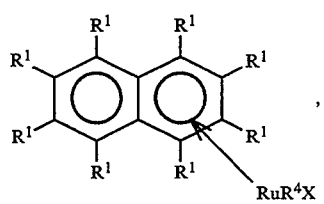

or

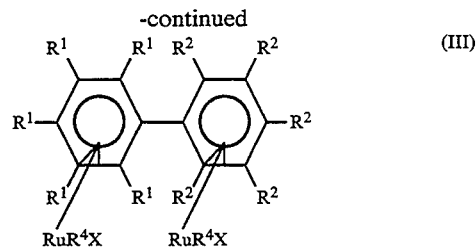

wherein:
each $R^1$ and each $R^2$ is independently hydrogen, halogen or $R^3$;
$R^3$ is an inert monovalent radical having a Hammett sigma constant which is greater than $-0.35$ and less than $-0.12$;
$R^4$ is cyclopentadienyl or pentamethylcyclopentadienyl;
X is perfluoroalkylsulfonate or hexafluorophosphate; and provided that:
at least three of $R^1$ and at least three of $R^2$ are halogen;
and no more than two of $R^1$, and no more than two of $R^2$, are $R^3$.

This invention also concerns a process for the production of aromatic ethers and thioethers, comprising, contacting a pi-polyhaloarene complex of the formula

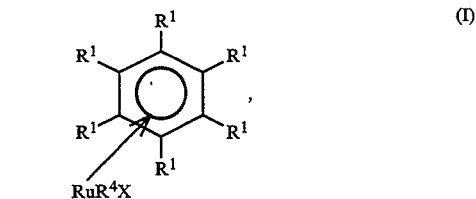

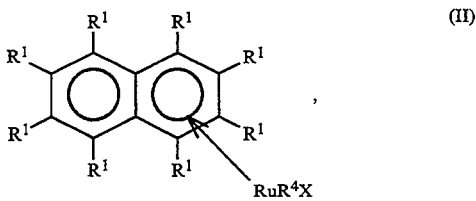

or

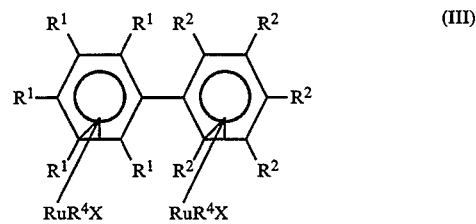

with a second compound of the formula

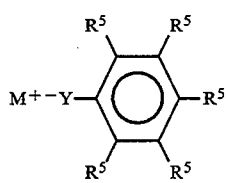

wherein:

each $R^1$ and each $R^2$ is independently hydrogen, halogen or $R^3$;

$R^3$ is an inert monovalent radical having a Hammett sigma constant which is greater than $-0.35$ and less than $-0.12$;

$R^4$ is cyclopentadienyl or pentamethylcyclopentadienyl;

X is perfluoroalkylsulfonate or hexafluorophosphate;

M is an alkali metal cation;

Y is oxygen or sulfur;

each $R^5$ is independently hydrogen, halogen, amino, alkyl or alkoxy;

and provided that:

at least three of $R^1$ and at least three of $R^2$ are halogen;

no more than two of $R^1$, and no more than two of $R^2$, are $R^3$; and at least 1 of $R^5$ is halogen or amino; and at least 3 of $R^5$ are hydrogen, alkyl or alkoxy.

This invention further concerns a polyfunctional pi-arene complex of the formula

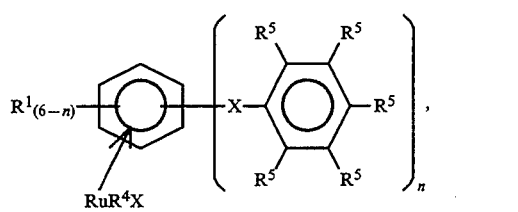

(V)

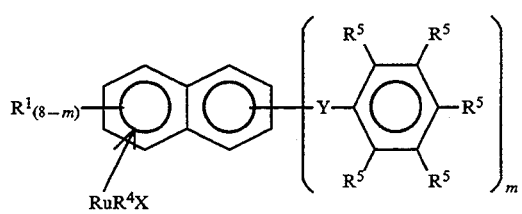

(VI)

or

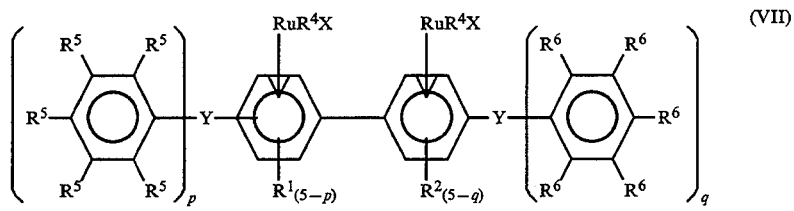

(VII)

wherein:

n is 2, 3, 4 or 5;

m is an integer of 2 through 7;

p and q are independently an integer of 1 through 4;

each $R^5$ and each $R^6$ is independently hydrogen, halogen, alkyl, alkoxy or amino;

$R^4$ is cyclopentadienyl or pentamethylcyclopentadienyl;

X is perfluoroalkylsulfonate or hexafluorophosphate;

Y is oxygen or sulfur;

each $R^1$ and each $R^2$ is independently hydrogen, halogen or $R^3$;

$R^3$ is an inert monovalent radical having a Hammett sigma constant which is greater than $-0.35$ and less than $-0.12$; and provided that at least one of $R^5$ and one of $R^6$ is amino or halogen, and at least 3 of $R^5$ and 3 of $R^6$ are hydrogen, alkyl or alkoxy.

DETAILS OF THE INVENTION

The pi-polyhaloarene complexes (PPAC) disclosed herein are useful in the preparation of the polyfunctional pi-arene complexes of formulae V, VI and VII which are useful as monomers and crosslinking agents in condensation polymerization. In the formulas for ruthenium pi-arene complexes herein, the symbol "→" indicates a ruthenium atom (or cation) coordinated to an arene (aromatic) ring, thus being a pi-arene complex.

Complexes I, II, III, and IV are prepared by reacting the corresponding haloaromatic with a ruthenium compound which can undergo ligand exchange reactions, i.e., $R^4$ Ru $(CH_3CN)_3$, $SO_3CF_3$. The reaction occurs in a relatively polar solvent, for example tetrahydrofuran, at 60°–80° C. for 4–40 hours, see Examples 1, 2, and 3.

In the PPACs of the present invention, the halogen, in $R^1$ and $R^2$, is fluorine, chlorine, bromine, and/or iodine. It is preferred if the halogen is fluorine, chlorine and/or bromine, more preferred if it is fluorine and/or chlorine, and especially preferred if it is chlorine. More than one type of halogen may be present in a PPAC. It is preferred if 3 or 4 of $R^1$ and $R^2$ attached to each aromatic system are halogen. In a preferred PPAC $R^4$ is pentamethylcyclopentadienyl. In another preferred form, X is perfluoroalkylsulfonate wherein the perfluoroalkyl group contains 1 to 8 carbon atoms, and more preferred if X is trifluoromethanesulfonate, "triflate". It is also preferred if $R^3$ is alkyl or alkoxy containing up to 20 carbon atoms. The preferred PPACs described in this paragraph are also preferred in the process for the production of aromatic ethers and thioethers.

The group $R^3$ is a group that does not interfere with the formation of the ruthenium pi-arene complex or with the nucleophilic substitution process (see below).

This group is chosen from those which have Hammett sigma (para) constant of more than −0.35 but less than −0.12, preferably more than −0.25 and less than −0.17. Examples of $R^3$ are alkyl and alkoxy. Such sigma constants are known to one skilled in the art, see for instance H. H. Jaffe, Chem. Rev., vol. 53, p. 191–261 (1953), especially Table 7.

The "second compound" of the process to make aromatic ethers or thioethers is a phenoxide or thiophenoxide salt of an alkali metal cation ($M^+$). It is preferred if the alkali metal is potassium. In the thiophenoxide or phenoxide it is preferred if, on each ring, one of $R^5$ is halo or amino and the rest of $R^5$ are hydrogen. It is more preferred if, on each ring, one of $R^5$ is amino and the other of $R^5$ are hydrogen.

The process is preferably carried out in solution, useful solvents being aprotic (less acidic than phenols and thiophenols) and relatively polar. Suitable solvents include tetrahydrofuran, acetonitrile and dimethylsulfoxide. It is preferred to carry out the process at 25° C. to 80° C., more preferably 25° C. to 60° C. Since some of the reactants are sensitive to water and/or oxygen, it is preferred to carry out the process under a dry inert gas such as nitrogen or argon. The ingredients are preferably mixed initially, and it is preferred to agitate the process gently. The process may be carried out so that one, some or all of the halogen atoms in the PPAC are reacted in the process. When all of the halogen atoms are not reacted, some of the halogen atoms originally contained in the starting PPAC will be present in the product.

The product of the process is a polyfunctional pi-arene complex of formulae V, VI and VII. In the polyfunctional pi-arene complex it is preferred that n is 3 or 4, that m is 3 or 4, and that p and q are each independently 2 or 3. It is also preferred that one of $R^5$ and one of $R^6$ in each ring is halogen or amino, more preferred that it is amino, and all of the remaining $R^5$ and $R^6$ are hydrogen. It is preferred that all of $R^1$ and all of $R^2$ are hydrogen.

In the following Examples, Cp* is pentamethylcyclopentadienyl.

EXAMPLE 1

Synthesis of Cp*Ru(1,3,5-trichlorobenzene), SO₃CF₃

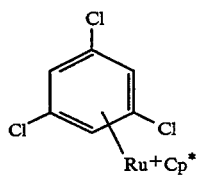

A 100 mL Schlenk flask was charged with 1,3,5-trichlorobenzene (1.64 g, 9.05 mmol, 15% excess) and Cp*Ru(CH₃CN)₃, SO₃CF₃ (4.00 g, 7.87 mmol) in THF (70 mL). The reaction was stirred and heated at reflux for 16 h. Addition of diethyl ether (45 mL) to the solution precipitated a white solid that was isolated by filtration and washed twice with 10 mL of ether and dried in vacuo.

¹H NMR (d₆-DMSO): 7.21 (s, 3H, arene), 1.88 (s, 15H, CH3) ppm; ¹³C NMR (d₆-DMSO): 102.5, 98.7, 89.1, 8.5 ppm; MS (positive FAB) calcd m/z cation 417, found m/z 417; Anal. Calcd for C₁₇H₁₈Cl₃RuSO₃F₃: C, 36.02, H, 3.20. Found: C, 35.89, H, 3.12. Yield: 72.5%.

EXAMPLE 2

Synthesis of Cp*Ru(1,2,4,5-tetrachlorobenzene), SO₃CF₃

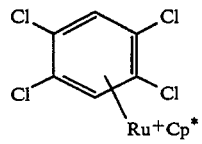

The procedure was the same as described for Example 1 but using ca. 30% excess 1,2,4,5-tetrachlorobenzene.

1H NMR (d₆-DMSO): 7.66 (s, 2H, arene), 1.82 (s, 15H, CH3) ppm; ¹³C NMR (d₆-DMSO): 130.2, 99.3, 88.5, 8.0 ppm; MS (positive FAB) calcd m/z cation 450.9, found m/z cation 450.9; Anal. Calcd for C₁₇H₁₇Cl₄RuSO₃F₃: C, 33.96, H, 2.85. Found: C, 33.83, H, 2.66. Yield: 78%.

EXAMPLE 3

Synthesis of Cp*Ru(Hexachlorobenzene), SO₃CF₃

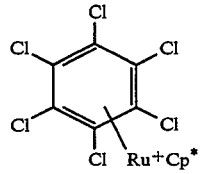

A 100 mL Schlenk flask was charged with hexachlorobenzene (1.40 g, 4.93 mmol, 2.5 equiv) and Cp*Ru(CH₃CN)₃, SO₃CF₃ (1.0 g, 1.97 mmol) in dioxane (25 mL) or diglyme (25 mL). The reaction mixture was stirred and heated at 80° C. for 3 days. After cooling the reaction mixture to 25° C. the solids that precipitated were collected by filtration and washed with toluene (3×50 mL) to remove excess unreacted hexachlorobenzene. The remaining solids were collected and dried in vacuo.

¹H NMR (d₆-DMSO): 1.65 (s, CH3); ¹³C NMR (d₆-DMSO): 104.0, 100.8, 7.2 ppm; MS (positive FAB) calcd m/z cation 519, found m/z cation 519; Anal. Calcd for: C, 30.47, H, 2.26. Found: C, 30.42, H, 2.14.

EXAMPLE 4

Synthesis of Cp*Ru(1,3,5-tris (4-aminophenoxy)benzene), SO₃CF₃

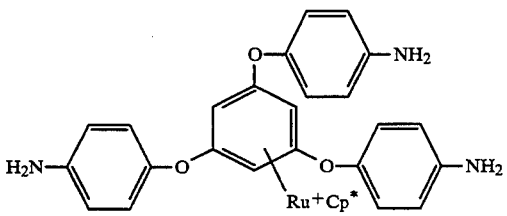

A 100 mL Schlenk flask charged with Cp*Ru(1,3,5-trichlorobenzene), (SO₃CF₃) (0.30 g, 0.53 mmol) and potassium p-aminophenoxide (0. 257 g, 1.75 mmol) in acetonitrile (20 mL) was stirred at 25° C. for 1 h. To ensure complete substitution, the reaction was warmed at 60° C. for 1 h. The solvent was removed in vacuo, the residue was dissolved in methylene chloride (15 mL), extracted with water (2×20 mL), and the organic layer was dried over MgSO₄. After filtration, the solvent was removed in vacuo and the residue was dissolved in acetonitrile (5–10 mL). Addition of diethyl ether (15 mL) precipitated a white solid that was isolated by filtration and dried in vacuo.

$^1$H NMR (d$_6$-DMSO): 6.86 (d, J=8.9 Hz, 6H, Ar H), 6.56 (d, J=8.9 Hz, 6H, Ar H), 5.79 (s, 3H, arene), 1.92 (s, 15H, CH3) ppm; $^{13}$C NMR (d$_6$-DMSO): 146.6, 143.9, 129.0, 120.3, 114.7, 94.9, 68.8, 10.0 ppm; MS (positive FAB) calcd m/z cation 636.2, found m/z cation 636.2; Anal. Calcd for C$_{35}$H$_{36}$N$_3$O$_6$SF$_3$Ru: C, 53.57, H, 4.62, N, 5.35. Found: C, 53.02, H, 4.41, N, 5.29.

EXAMPLE 5

Synthesis of Cp*Ru (1,2,4,5-tetrakis (4-aminophenoxy)benzene), SO₃CF₃

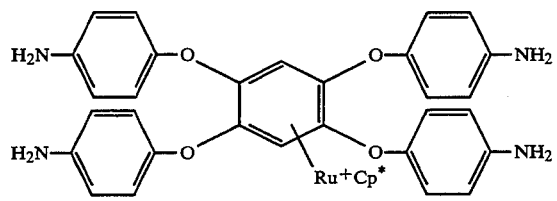

The procedure is the same as described for Example-4 using Cp*Ru(1,2,4,5-tetrachlorobenzene), SO₃CF₃ and potassium 4-aminophenoxide in acetonitrile solvent.

$^1$H NMR (d$_6$-DMSO): 6.88 (d, J=8.9 Hz, 8H, Ar H), 6.53 (d, J=8.9 Hz, 8H, Ar H), 5.94 (s, 2H, arene), 1.91 (s, 15H, CH3) ppm; $^{13}$C NMR (d$_6$-DMSO): 145.8, 118.9, 118.0, 114.6, 95.4, 73.0, 9.5 ppm; MS (positive FAB) calcd m/z cation 743; found m/z cation 743; Anal. Calcd for C$_{41}$H$_{41}$O$_7$SN$_4$F$_3$Ru: C, 55.21, H, 4.63, N, 6.28. Found: C, 54.02, H, 4.16, N, 6.14.

EXAMPLE 6

Synthesis of Cp*Ru (1,3,5-tris (4-chlorophenoxy)benzene), SO₃CF₃

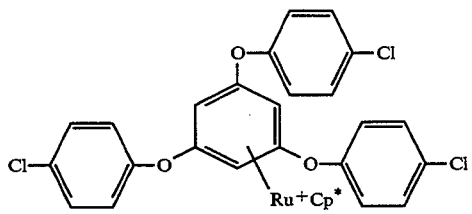

The procedure is the same as described for Example 4 using potassium 4-chlorophenoxide in acetonitrile solvent.

$^1$H NMR (d$_6$-DMSO): 7.53 (d, J=9.1 Hz, 6H, Ar H), 7.30 (d, J=9.1 Hz, 6H, Ar H), 6.49 (s, 3H, arene), 1.96 (s, 15H, CH3) ppm; $^{13}$C NMR (d$_6$-DMSO): 154.4, 129.9, 128.6, 125.8, 119.9, 96.5, 73.9, 9.5 ppm; MS (positive FAB) calcd m/z cation 693, found m/z cation 693; Anal. Calcd for C$_{35}$H$_{30}$O$_6$SCl$_3$F$_3$Ru: C, 49.86, H, 3.56. Found: C, 49.61, H, 3.27.

EXAMPLE 7

Synthesis of Cp*Ru (1,2,4,5-tetrakis (4-chlorophenoxy)benzene), SO₃CF₃

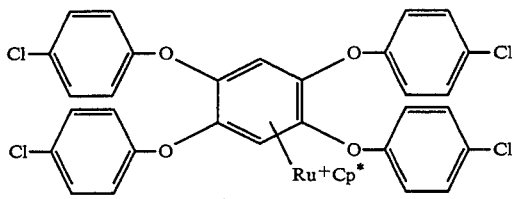

The procedure is the same as described for Example 4 using Cp*Ru (1,2,4,5-tetrachlorobenzene), SO₃CF₃ and potassium 4-chlorophenoxide in acetonitrile solvent.

$^1$H NMR (d$_6$-DMSO): 7.44 (d, J=9.1 Hz, 8H, Ar H), 7.31 (d, J=9.1 Hz, 8H, Ar H), 7.00 (s, 2H, arene), 1.97 (s, 15H, CH3) ppm; $^{13}$C NMR (d$_6$-DMSO): 154.9, 129.6, 128.2, 118.7, 117.5, 97.3, 76.6, 9.1 ppm; MS (positive FAB) calcd m/z cation 819; found m/z cation 819; Anal. Calcd for C$_{41}$H$_{33}$O$_7$SCl$_4$F$_3$Ru: C, 50.79, H, 3.43. Found: C, 50.23, H, 3.36.

EXAMPLE 8

Synthesis of Cp*Ru (1,3,5-tris (4-fluorophenoxy)benzene), SO₃CF₃

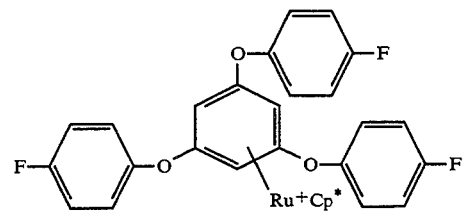

The procedure is the same as described for Example 4 using potassium 4-fluorophenoxide in acetonitrile solvent.

$^1$H NMR (d$_6$-DMSO): 7.32–7.29 (m, 12H, Ar H), 6.32 (s, 3H, arene), 1.96 (s, 15H, CH3) ppm; $^{13}$C NMR (d$_6$-DMSO): 158.9 (d, $^1J_{CF}$=241.2 Hz), 151.6, 126.7, 120.3 (d, $^3J_{CF}$=8.6 Hz), 116.9 ($^2J_{CF}$=23.7 Hz), 96.3, 72.9, 9.7 ppm; MS (positive FAB) calcd m/z cation 645, found m/z cation 645; Anal. Calcd for C$_{35}$H$_{30}$O$_6$SF$_6$Ru: C, 52.96, H, 3.81. Found: C, 52.95, H, 3.19.

What is claimed is:

1. A pi-polyhaloarene complex of the formula

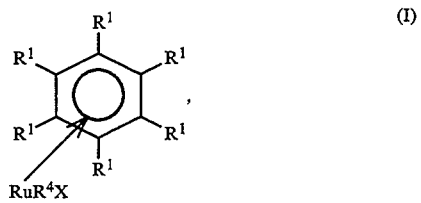

(I)

-continued

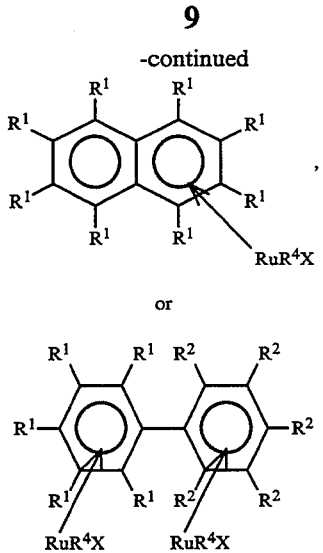

wherein:
- each $R^1$ and each $R^2$ is independently hydrogen, halogen $R^3$;
- $R^3$ is an inert monovalent radical having a Hammett sigma constant which is greater than $-0.35$ and less than $-0.12$;
- $R^4$ is cyclopentadienyl or pentamethylcyclopentadienyl;
- X is perfluoroalkylsulfonate or hexafluorophosphate;

and provided that:
- at least three of $R^1$ and at least three of $R^2$ are halogen;
- and no more than two of $R^1$, and no more than two of $R^2$, are $R^3$.

2. The pi-polyhaloarene complex as recited in claim 1 wherein said halogen is independently selected from the group consisting of fluorine, chlorine, and bromine.

3. The pi-polyhaloarene complex as recited in claim 2 wherein said halogen is independently selected from the group consisting of fluorine and chlorine.

4. The pi-polyhaloarene complex as recited in claim 3 wherein said halogen is chlorine.

5. The pi-polyhaloarene complex as recited in claim 1 wherein $R^3$ is an inert monovalent radical having a Hammett sigma constant which is greater than $-0.25$ and less than $-0.17$.

6. The pi-haloarene complex as recited in claim 5 wherein $R^3$ is selected from the group consisting of alkyl and alkoxy.

7. The pi-haloarene complex as recited in claim 1 wherein $R^4$ is pentamethylcyclopentadienide.

8. The pi-haloarene complex as recited in claim 1 wherein X is perfluoroalkylsulfonate wherein the perfluoroalkyl group contains 1–8 carbon atoms.

9. The pi-haloarene complex as recited in claim 8 wherein X is trifluoromethanesulfonate.

10. The pi-polyhaloarene complex as recited in claim 1 of the formula

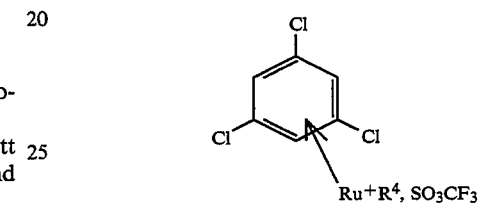

wherein $R^4$ is pentamethylcyclopentadienyl.

11. The pi-polyhaloarene complex as recited in claim 1 of the formula

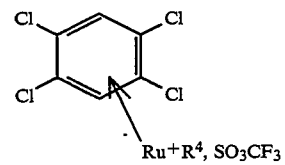

wherein $R^4$ is pentamethylcyclopentadienyl.

* * * * *